(12) United States Patent
Hütter

(10) Patent No.: US 6,935,776 B2
(45) Date of Patent: Aug. 30, 2005

(54) SAMPLE HOLDER FOR DIFFERENTIAL THERMAL ANALYSIS

(75) Inventor: Thomas Hütter, Niederrohrdorf (CH)

(73) Assignee: Mettler-Toledo GmbH, Greifensee (CH)

( * ) Notice: Subject to any disclaimer, the term of this patent is extended or adjusted under 35 U.S.C. 154(b) by 0 days.

(21) Appl. No.: 10/458,830

(22) Filed: Jun. 9, 2003

(65) Prior Publication Data

US 2003/0231693 A1 Dec. 18, 2003

(30) Foreign Application Priority Data

Jun. 18, 2002 (DE) ......................................... 102 27 182

(51) Int. Cl.⁷ .......................... G01N 25/00; H01L 35/28
(52) U.S. Cl. ............................ 374/12; 374/13; 136/225
(58) Field of Search .............................. 374/10, 12, 13, 374/179; 136/231, 225

(56) References Cited

U.S. PATENT DOCUMENTS

| | | | |
|---|---|---|---|
| 5,033,866 A | * 7/1991 | Kehl et al. | 374/179 |
| 5,288,147 A | * 2/1994 | Schaefer et al. | 374/10 |
| 5,842,788 A | 12/1998 | Danley et al. | |
| 6,146,012 A | 11/2000 | Nakamura et al. | |
| 6,318,890 B1 | * 11/2001 | Hutter et al. | 374/10 |
| 6,390,669 B1 | 5/2002 | Nakamura et al. | |
| 6,508,585 B2 | * 1/2003 | Nakamura et al. | 374/12 |
| 2002/0021740 A1 | 2/2002 | Danley | |

FOREIGN PATENT DOCUMENTS

| | | |
|---|---|---|
| CH | 690627 | 11/2000 |
| EP | 0962763 | 12/1999 |
| EP | 1215484 | 6/2002 |

* cited by examiner

Primary Examiner—Diego Gutierrez
Assistant Examiner—Mirellys Jagan
(74) Attorney, Agent, or Firm—Friedrich Kueffner

(57) ABSTRACT

A sample holder for differential thermal analysis has a substrate with a planar surface provided with a sample position for a sample material and a reference position for reference material. The substrate allows heat flow between a heat source thermally coupled to the sample holder and the sample and reference positions. A first thermoelement arrangement in the area of the sample and reference positions is provided for supplying a thermoelectric signal corresponding to a differential between the temperatures at the sample and reference positions. First connectors are formed on the substrate for tapping the thermoelectric signal corresponding to the temperature differential. A second thermoelement arrangement provides a thermoelectric signal corresponding to an absolute temperature of the sample and reference positions. Second connectors are provided on the substrate for tapping the thermoelectric signal corresponding to the absolute temperature.

9 Claims, 3 Drawing Sheets

SAMPLE HOLDER FOR DIFFERENTIAL THERMAL ANALYSIS

BACKGROUND OF THE INVENTION

1. Field of the Invention

The invention relates to a sample holder for differential thermal analysis, comprising a substrate having on a planar surface a sample position for receiving a sample material and a reference position for receiving a reference material, through which substrate a heat flow between a heat source, thermally coupled to the sample holder, and the sample position and the reference position can be guided, respectively, comprising a thermoelement arrangement in the area of the sample position and in the area of the reference position for supplying a thermoelectric signal corresponding to the differential between the two temperatures at the sample position and the reference position, and comprising connectors formed on the substrate where the thermoelectric signal corresponding to the differential between the two temperatures can be tapped.

2. Description of the Related Art

Such a sample holder is disclosed in DE 39 16 311 A1. The thermoelectric signal which is supplied by the thermoelement arrangement corresponds to the temperature differential between the sample position and the reference position. As is well known, this temperature differential is a measure for the difference between the two heat flows which are generated between a heat source coupled to the sample holder and the sample position or the reference position. In an ideal situation of complete thermal symmetry, the difference between these two heat flows is exactly zero when neither at the sample position nor at the reference position a sample material or a reference material is present. In this ideal situation, the sample holder loaded with the sample material and the reference material then supplies the heat flow corresponding to the sample material relative to the reference material that is selected to be thermally inert; this heat flow differential is the basis for the further thermal analytic evaluation. For this ideal situation of absolute thermal symmetry, the absolute temperatures at the sample position or at the reference position must not be recorded. Instead, it is sufficient to measure the absolute temperature of the heat source coupled to the sample holder and to control it according to a temperature program desired for the thermal analytic assay.

In practice, even for the most careful construction of the sample holder, a complete thermal symmetry between sample position and reference position cannot be achieved. Theoretical examinations of the thermal asymmetry considering the individual heat flows correlated with the sample position and the reference position, respectively, have shown that the asymmetries can be corrected computationally when, in addition to the temperature difference between the sample position and the reference position, additional temperature parameters are measured.

SUMMARY OF THE INVENTION

It is an object of the present invention to further develop a sample holder of the aforementioned kind such that, for a simple, reliable, and compact configuration, parameters for the correction of thermal asymmetries are made available.

In accordance with the present invention, this is achieved in that on the substrate, on at least one of the two positions, an additional thermoelement arrangement is provided for supplying a thermoelectric signal corresponding to the absolute temperature, and in that connectors are provided where the thermoelectric signal corresponding to the absolute temperature can be tapped.

On the sample holder according to the invention, in addition to the connectors where the thermoelectric signals corresponding to the differential between the temperatures at the sample location and the reference position are tapped, an additional thermoelement arrangement and connectors are therefore provided on the substrate where a thermoelectric signal is made available which represents the absolute temperature at one of the two positions, preferably at both positions. This additional temperature information can be used in order to correct computationally thermal symmetry deviations, which cannot be detected simply by the temperature differential measurement between the sample position and the reference position and which, when not recorded, lead to an evaluation error because, as a result of the asymmetry, the temperature differential does not correspond precisely to the differential between the two heat flows at the sample position and the reference position.

An advantageous configuration of the inventive principle resides in that the thermoelement arrangement designed for providing the thermoelectric signal corresponding to the differential between the two temperatures has a row of thermocontacts correlated with the sample position and the reference position, respectively, wherein the thermocontacts are composed of two different thermoelement materials and are connected serially to form a thermocolumn, wherein the thermocontacts are alternatingly arranged on two circles of different radii centrally positioned relative to the sample position and the reference position, and wherein the thermoelement arrangement for providing the thermoelectric signal corresponding to the absolute temperature has a circularly delimited area of a first thermoelement material surrounded concentrically by a corresponding row of thermocontacts from where a connecting area extends to one of the connectors provided on the surface of the substrate.

In this configuration, the thermal symmetry deviations resulting from the configuration of the two thermocolumns, which surround the sample position and the reference position with a circular ring shape, are minimized as much as possible so that the corrections to be applied as a result of the additionally measured absolute temperatures can be small. Each one of the two thermocolumns uses the fact that the heat flow is proportional to the temperature differential between two temperature measurement points spaced apart from one another along the heat flow path. In approximation, the heat flows correlated with the sample position and the reference position, respectively, are radially symmetrically arranged relative to the centers of the sample position and the reference position in the case of a suitable coupling to the heat source. Accordingly, the thermocontacts arranged on the radially inner circle and the radially outer circle provide suitable temperature measurement points on the heat flow-path wherein the serial connection of the thermoelectric voltages occurring between them in the thermocolumn results in a total thermoelectric voltage which very closely approximates the corresponding heat flow. In this connection, it is beneficial with respect to the thermal symmetry that the thermoelement arrangement serving for measuring the absolute temperature is also substantially radially symmetrical within the radially inner circle of the thermocontacts in that the first thermoelement material applied onto the substrate is circularly delimited and concentric to the circles of the thermocontacts of the thermocolumns.

Preferably, this first thermoelement material is of a circular ring shape so that it has a central cutout.

Expediently, generating and tapping of the thermoelectric voltage corresponding to the absolute temperature is achieved in that, on the circularly delimited area of the first thermoelement material, a thermocontact of a second thermoelement material that is different from the first thermoelement material is provided that extends to one of the connectors provided on the substrate.

According to another embodiment, simplification and improved utilization of the spatial conditions on the sample holder are provided in that on the substrate a connection between the second thermoelement materials of the sample position and the reference position is provided and connected to a common connector. Between this common connector and the two connectors of the sample position and of the reference position connected to the first thermoelement material, a thermoelectric signal can be tapped which corresponds to the absolute temperature of the sample position and the reference position, respectively.

Moreover, with respect to minimizing the connecting structure to be arranged on the substrate, it is advantageous to form on the substrate a connection between two electrically equivalent ends of the thermocolumns correlated with the sample position and the reference position, and the two other ends of the thermocolumns are connected, respectively, to the connectors provided for tapping the thermoelectric signal corresponding to the differential between the two temperatures. In this configuration, the two thermocolumns are connected electrically opposed so that the thermoelectric signal corresponding to the differential of the temperatures at the sample position and at the reference position is obtained at the two connectors, respectively.

In addition, for the evaluation and correctional computation, it may be desirable to be able to tap the individual output signals of the two thermocolumns corresponding in approximation to the individual heat flows. For a minimization of the connecting structure on the substrate required for this, it is advantageous that the connection is connected with a common connector formed on the substrate. Between this common connectors and the ends of the two thermocolumns guided to the corresponding connectors, it is thus possible to tap separately the output signal of both thermocolumns, respectively.

In the context of the invention, it is particularly provided that the thermoelement arrangements formed on the substrate are configured as thick films. The application of thick film technology for manufacturing the thermoelement arrangements on the substrate is explained in detail in the aforementioned DE 39 16 311 A1 and the German patent DE 39 16 311 C2 issued thereon, including discussion of the advantages obtained thereby. The disclosure of the two documents is herewith included by reference into the present application. In particular, the thick film technology in a simple way solves the problem of insulation of the individual structural elements of the thermoelement arrangement to the exterior, i.e., relative to the sample crucibles and reference crucibles placed onto the sample position and the reference position, as well as the mutual insulation of overlapping parts of the structures, as they occur between structural elements of the thermocolumns and connections of the thermoelement arrangements for measuring the absolute temperature and their connectors.

With respect to the desired thermal inertness and resistance of the sample holder, it is advantageous that the substrate is a ceramic material.

BRIEF DESCRIPTION OF THE DRAWING

Further features, advantages, and details result from the following description in which the invention will be explained in more detail with reference to the drawings.

In the drawing.

DESCRIPTION OF THE PREFERRED EMBODIMENTS

Figure 1:
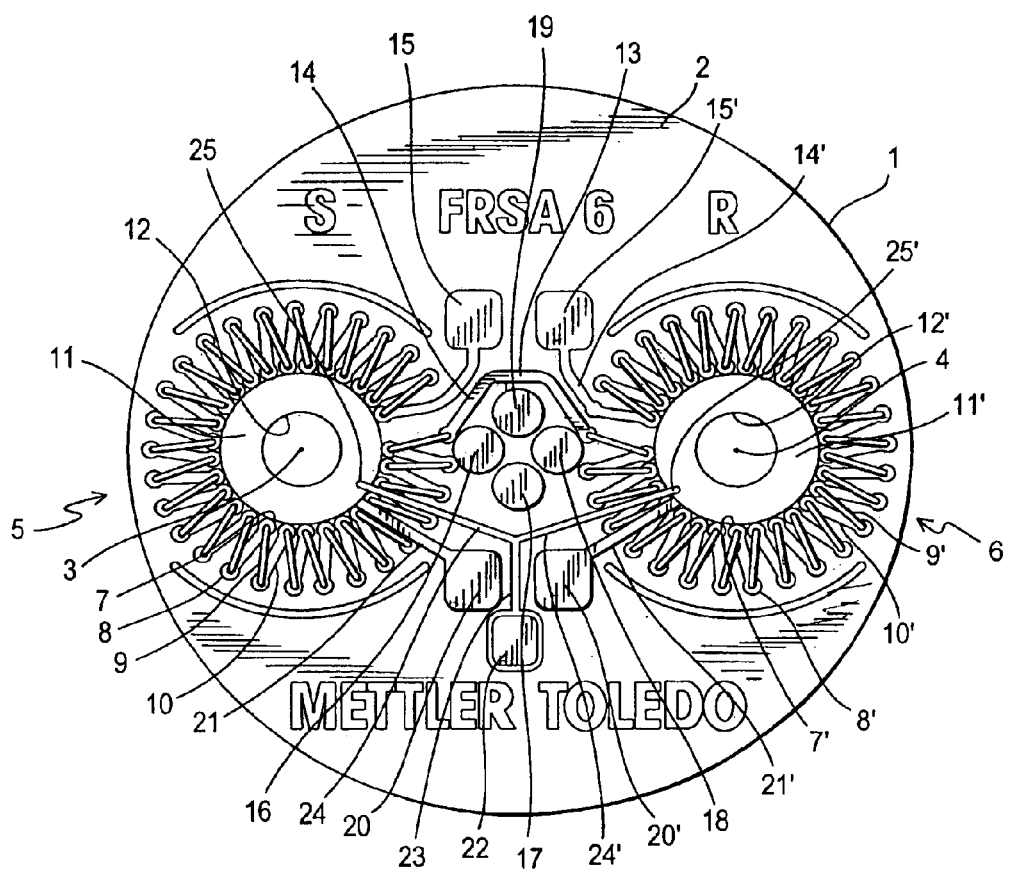
FIG. 1 is a plan view onto a first embodiment of the sample holder.

A circular ring-shaped ceramic substrate 1, which is illustrated in FIG. 1 in a plan view onto its planar surface 2, is provided with a structure applied by thick film technology which serves for supplying thermoelectric signals suitable for performing differential thermal analysis. On a line extending through the center point of the circular ring-shaped substrate 1, the centers 3 and 4 of a sample position 5 and a reference position 6 are provided at the same radial spacing to the center point.

The sample position 5 is surrounded by a thermocolumn comprised of series-connected thermocontacts which are arranged alternatingly at a smaller or greater radial spacing from the center 3. The thermocontacts 7 arranged at the smaller radial spacing as well as the thermocontacts 8 arranged at the greater radial spacing are positioned on circles concentric to the center 3, respectively. In the circumferential direction, the thermocontacts 8 arranged on the radially outer circle are centrally staggered, respectively, relative to the thermocontacts 7 arranged on the radially inner circle. Within the thermocolumn, the two different thermoelement materials in the form of the linear strips 9, 10 extend between the thermocontacts 7, 8 approximately radially.

Within the radially inner circle of the thermocontacts 7, at a smaller radial spacing thereto, a ring-shaped first thermoelement material 11 is provided on the substrate 1 in a central arrangement relative to the center 3 of the sample position 5. In the area surrounded by the inner ring periphery 12, the substrate 1 has an axially extending cutout.

The reference position 6 is provided with a structure symmetrically embodied to the structure of the sample position 5 relative to the center of the substrate 1. The reference numerals of the structure corresponding to those of the sample position 5 are provided with an apostrophe in FIG. 1, and the description provided above for the sample position 5 applies here as well.

Moreover, FIG. 1 shows that two electrically equivalent ends of the two thermocolumns are connected to one another by a connection 13 formed on the substrate 1. The two other ends are extended by means of connecting strips 14, 14' to a connecting area 15, 15'. The entire connecting and contacting structure 13, 14, 14', 15, 15' is mirror-symmetrical relative to a central vertical line onto the connecting line between the centers 3, 4. The connection 13 surrounds a central area of the ceramic substrate 1 in which axial passages 16, 17, 18, 19 are formed on the ceramic substrate 1; they have centers arranged in pairs and centrally symmetrically on the connecting line between the centers 3, 4 or the central vertical line extending vertically thereto. A thermal coupling member can be secured on these axial passages which serves as a thermal connection of the sample holder to a heat source.

On the side of the surface 2 of the substrate 1 that is opposed to the connection 13 and the connecting areas 15, 15' relative to the connecting line between the centers 3, 4, an additional connecting structure is formed. It has two connecting areas 20, 20' mirror-symmetrical relative to the central vertical line extending vertically to the connecting line between the two centers 3, 4 from where, also mirror-symmetrically to the central vertical line, connecting strips 21, 21' extend substantially radially to the first thermoelement material 11, 11' thus providing an electrical connection between the latter and the connecting areas 20, 20'. The required electrical insulation between this connecting structure and the thermoelement structures crossed thereby is taken into consideration in the thick film manufacturing process. Reference is being had to the corresponding disclosure in DE 39 16 311 A1 and DE 39 16 311 C2.

On the central vertical line, on the side of the substrate 1 provided with the connecting areas 20, 20', a common connector 22 is centrally arranged from where a connecting member 23 extends, along the central vertical line and through the two connecting areas 20, 20', to a Y-shaped branch from where the connecting member 23 extends with two strip-shaped branches 24, 24', mirror-symmetrically to the central vertical line, with insulation across the thermocolumn structure into the annular first thermoelement materials 11, 11'. The connecting member 23 and its branches 24, 24' are comprised of a second thermoelement material which forms a thermocontact 25, 25' together with the first thermoelement material 11, 11', respectively. It can be seen easily that with this arrangement the thermoelectric signal occurring at the thermocontact 25 can be tapped between the common connector 22 and the connector area 20 while the thermoelectric signal occurring at the thermocontact 25' can be tapped between the common connector 22 and the connecting area 20'.

Figure 2:
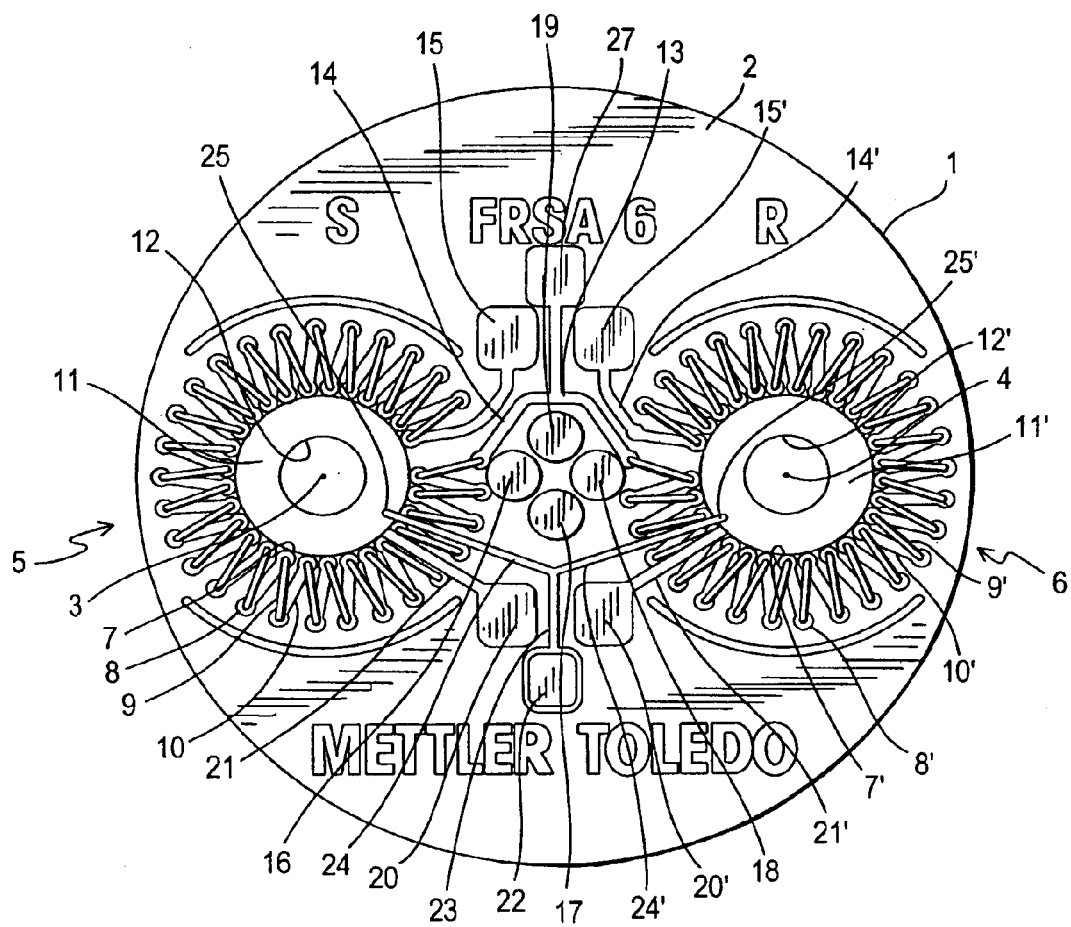
FIG. 2 is a plan view onto a second embodiment of the sample holder.
Figure 3:
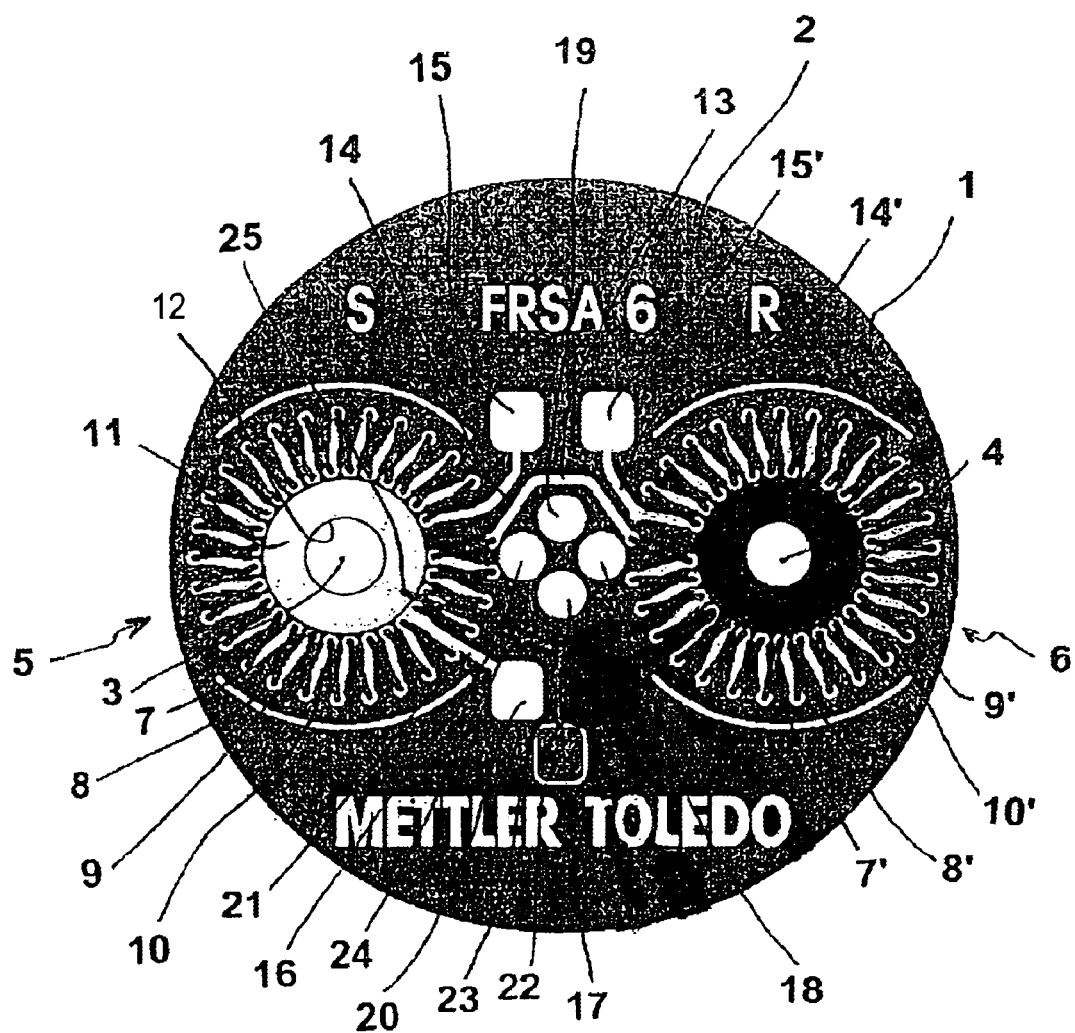
FIG. 3 is a plan view showing a sample holder having only one second thermoelement arrangement and only one set of second connectors.

The embodiment illustrated in FIG. 2 has, in addition to the features of the embodiment of FIG. 1, a connecting stay 26 branching off the connection 13 and extending along the central vertical line of the connecting line of the two centers 3, 4 which extends to a common connector 27 which is arranged mirror-symmetrically relative to the common connector 22 with respect to the connecting line between the centers 3, 4. In other respects, the embodiment of FIG. 2 corresponds to that of FIG. 1. Accordingly, identical reference numerals are used, and reference is being had to the description of FIG. 1. While in FIG. 1 only the difference between the thermoelectric voltages provided by the thermocolumns at the connectors 15, 15' is available, in the embodiment of FIG. 2 between the common connector 27 and the connecting area 15 or 15' the thermoelectric output signals of the two thermocolumns can be tapped separately, respectively.

It is apparent that in both embodiments the structures arranged on the planar surface 2 of the substrate 1 are optimized as much as possible with respect to thermal symmetry between the sample position 5 and the reference position 6. For detecting remaining symmetry deviations, the embodiments illustrated in FIGS. 1 and 2 provide, in addition to the temperature differential occurring between the connectors 15, 15', additional thermoelectric signals which correspond to the absolute temperature at the sample position 5 or the reference position 6. These absolute temperature signals can be tapped between the common connector 22 and the connecting areas 20 and 20'. In the embodiment illustrated in FIG. 2, the output signals of the two thermocolumns can aditionally be tapped separately between the common connector 27 and the connecting areas 15, 15'.

While specific embodiments of the invention have been shown and described in detail to illustrate the inventive principles, it will be understood that the invention may be embodied otherwise without departing from such principles.

What is claimed is:

1. A sample holder for differential thermal analysis, comprising:

a substrate having a planar surface provided with a sample position for receiving a sample material and provided with a reference position for receiving a reference material;

wherein the substrate is configured to allow a neat flow between a heat source to be thermally coupled to the sample holder and the sample position and the reference position;

a first thermoelement arrangement in the area of the sample position and in the area of the reference position for supplying a first thermoelectric signal corresponding to a differential between a first temperature at the sample position and a second temperature at the reference position;

first connectors formed on the substrate for connecting to the first thermal element arrangement;

wherein the first thermoelectric signal corresponding to the differential between the first and second temperatures is tapped at the first connectors;

a second thermoelement arrangement providing a second thermoelectric signal corresponding to an absolute temperature of at least one of the sample position and the reference position;

second connectors provided on the substrate for connecting to the second thermal element arrangement;

wherein the second thermoelectric signal corresponding to the absolute temperature is tapped at the second connectors;

the first thermoelement arrangement has a row of first thermocontacts correlated with the sample position and the reference position, respectively;

the first thermocontacts are composed of two different thermoelement materials and are connected serially to form a thermocolumn at the sample position and at the reference position, respectively;

the first thermocontacts are alternatingly arranged on two circles of different radii centrally positioned relative to the sample position and the reference position, respectively; and the second thermoelement arrangement is a circularly delimited area of a first thermoelement material surrounded concentrically by a corresponding row of the first thermocontacts at least at one of the sample position and the reference position, wherein a connecting area extends from the first thermoelement material to one of the second connectors provided on the surface of the substrate.

2. The sample holder according to claim 1, wherein the circularly delimited area of the first thermoelement material has a circular ring shape.

3. The sample holder according to claim 1, wherein the first and second thermoelement arrangements are formed as thick films.

4. The sample holder according to claim 1, wherein the substrate is a ceramic material.

5. The sample holder according to claim 1, wherein on the circularly delimited area of the first thermoelement material a second thermocontact comprised of a second thermoelement material different from the first thermoelement material is formed, wherein the second thermocontact extends to another of the second connectors.

6. The sample holder according to claim 5, comprising a connection provided on the substrate and connecting the second thermocontact of the sample position and of the reference position, wherein the connection is guided to one of the second connectors which forms a common connector.

7. The sample holder according to claim 1, comprising a connection provided on the substrate and connecting two electrically equivalent first ends of the thermocolumns of the sample position and the reference position, wherein second ends of the thermocolumns are connected to the first connectors, respectively.

8. The sample holder according to claim 7, wherein the connection is connected to a common connector formed on the substrate.

9. A sample holder for differential thermal analysis, comprising:

a substrate having a planar surface provided with a sample position for receiving a sample material and provided with a reference position for receiving a reference material;

wherein the substrate is configured to allow a neat flow between a heat source to be thermally coupled to the sample holder and the sample position and the reference position;

a first thermoelement arrangement in the area of the sample position and in the area of the reference position for supplying a first thermoelectric signal corresponding to a differential between a first temperature at the sample position and a second temperature at the reference position;

first connectors formed on the substrate for connecting to the first thermal element arrangement;

wherein the first thermoelectric signal corresponding to the differential between the first and second temperatures is tapped at the first connectors;

a second thermoelement arrangement providing a second thermoelectric signal corresponding to an absolute temperature of at least one of the sample position and the reference position;

wherein the second thermoelement arrangement comprises a circularly delimited area of a first thermoelement material in a central arrangement relative to the center of at least one of the sample position and the reference position, and a second thermoelement material different from the first thermoelement material to forming a thermocontact with said first thermoelement material;

second connectors provided on the substrate on at least one of the sample position and the reference position and connected to the second thermoelement material;

wherein the second thermoelectric signal corresponding to the absolute temperature is tapped at the second connectors.

* * * * *